United States Patent
Dejneka et al.

(10) Patent No.: US 7,241,629 B2
(45) Date of Patent: Jul. 10, 2007

(54) DETECTABLE LABELS, METHODS OF MANUFACTURE AND USE

(75) Inventors: Matthew J. Dejneka, Corning, NY (US); Joydeep Lahiri, Painted Post, NY (US); Uwe R. Muller, Painted Post, NY (US); Cameron W. Tanner, Horseheads, NY (US); Patrick D. Tepesch, Corning, NY (US)

(73) Assignee: Corning Incorporated, Corning, NY (US)

( * ) Notice: Subject to any disclaimer, the term of this patent is extended or adjusted under 35 U.S.C. 154(b) by 693 days.

(21) Appl. No.: 10/027,286

(22) Filed: Dec. 20, 2001

(65) Prior Publication Data

US 2003/0119207 A1 Jun. 26, 2003

(51) Int. Cl.
*G01N 33/553* (2006.01)
*G05B 33/00* (2006.01)

(52) U.S. Cl. .......... 436/525; 436/501; 436/518; 435/6; 435/7.1; 530/387.1; 530/350; 250/484.2; 250/484.3; 385/123; 385/126; 385/121; 385/141

(58) Field of Classification Search .......... 435/6, 435/7.1; 530/387.1, 350; 250/484.2, 484.3; 385/123, 126, 121, 5, 141; 428/379, 365, 428/32.4; 501/54, 55, 37, 900, 42, 43, 9; 65/32.4; 436/501, 518, 525

See application file for complete search history.

(56) References Cited

U.S. PATENT DOCUMENTS

| | | | |
|---|---|---|---|
| 3,772,099 A | 11/1973 | Ryan et al. | 149/18 |
| 3,772,200 A | 11/1973 | Livesay | 252/301.1 |
| 3,861,886 A | 1/1975 | Meloy | 44/51 |
| 4,053,433 A | 10/1977 | Lee | 252/408 |
| 4,959,837 A * | 9/1990 | Fevrier et al. | 372/6 |
| 5,047,076 A * | 9/1991 | Cognolato et al. | 65/418 |
| 5,262,365 A * | 11/1993 | Oyobe et al. | 501/54 |
| 5,279,936 A * | 1/1994 | Vorpahl | 435/6 |
| 5,340,749 A * | 8/1994 | Fujiwara et al. | 436/526 |
| 5,405,754 A | 4/1995 | Van Hoegaerden | 436/523 |
| 5,480,582 A | 1/1996 | Pope | 252/301.4 |
| 5,668,659 A * | 9/1997 | Sakamoto et al. | 359/341.5 |
| 5,712,941 A * | 1/1998 | Imoto et al. | 385/126 |

(Continued)

FOREIGN PATENT DOCUMENTS

WO WO 88/03910 6/1988

(Continued)

OTHER PUBLICATIONS

"Functionalized Europium Oxide Nanoparticles Used As A Fluorescent Label In An Immunoassay For Atrazine" J. Feng, et al Analytical Chemistry 75 (19):5282-5286 Oct. 1, 2003.

(Continued)

*Primary Examiner*—Long V. Le
*Assistant Examiner*—Pensee T. Do
(74) *Attorney, Agent, or Firm*—Thomas R. Beall; Melissa K. Dobson

(57) ABSTRACT

Labels, methods of making labels and methods of using labels are disclosed. The labels can be manufactured using fiber drawing techniques or by shutter masking. The labels can be used for detecting the presence of an analyte in a sample and for detecting interactions of biomolecules.

15 Claims, 7 Drawing Sheets

U.S. PATENT DOCUMENTS

| | | | |
|---|---|---|---|
| 5,778,129 A * | 7/1998 | Shukunami et al. | 385/127 |
| 6,149,868 A | 11/2000 | Natan et al. | 422/82.05 |
| 6,159,686 A * | 12/2000 | Kardos et al. | 435/6 |
| 6,268,222 B1 | 7/2001 | Chandler et al. | 436/523 |
| 6,274,323 B1 | 8/2001 | Bruchez et al. | 435/6 |
| 6,312,914 B1 | 11/2001 | Kardos et al. | 435/6 |
| 6,326,125 B1 * | 12/2001 | Kakinuma et al. | 430/281.1 |
| 6,514,295 B1 | 2/2003 | Chandler et al. | 8/607 |
| 6,793,850 B2 * | 9/2004 | Ichikawa et al. | 252/511 |

FOREIGN PATENT DOCUMENTS

| | | |
|---|---|---|
| WO | WO 98/53093 | 11/1998 |
| WO | WO 00/63419 | 10/2000 |
| WO | WO 02/101358 | 12/2002 |

OTHER PUBLICATIONS

"Nanotechnology in biomedical applications" B. A. Holm, et al Molecular Crystals and Liquid Crystals 374: 589-598 2002, ABSTRACT.

"Flow Cytometry With Upconverting Phosphor Reporters" W. H. Wright, SRI International, Mar. 5, 1998, ABSTRACT.

"Rare earth-doped glass microbarcodes" M. J. Dejnika, et al, PNAS Jan. 21, 2003, vol. 100, No. 2, 389-393.

"Microbarcode Sorting Device" P. K. Yuen, et al, The Royal Society of Chemistry 2003, Jul. 10, 2003, 198-201.

Chemical and Engineering News, "How One Chemist's Outrage Sparked a Counterterrorism Invention," Jul. 24, 1997.

Microtrace, Inc. web page from www.microtaggant.com. 2001.

* cited by examiner

DETECTABLE LABELS, METHODS OF MANUFACTURE AND USE

FIELD OF THE INVENTION

This invention relates to detectable labels. More particularly, the present invention relates to labels, methods of manufacturing detectable labels and methods of using detectable labels.

BACKGROUND OF THE INVENTION

Miniaturized markers and indicators have found utility in a wide variety of areas, but they are of particular interest in biological and chemical assays. The development of multiplexing and miniaturization of chemical and biochemical assays has improved the analysis of samples in such areas as biomedical analysis, environmental science, pharmaceutical research, food and water quality control. For example, in the area of genomics, DNA arrays allow multiplexing and miniaturization of tests by providing a unique DNA target a unique address in the form of a position on the array in a small area (typically less than 100 microns in diameter) on the array surface. The total size of the surface and the spacing and size of the individual target determines the number of addresses available.

Microtiter plates also allow multiplexing and miniaturization of samples by providing many individual wells, each at a unique position. It is possible for each well to have a unique target and to be tested with a unique sample, which allows for the multiplexing of both targets and samples.

Another way of achieving miniaturization and multiplexing is through the use of miniaturized devices such as nanoparticles or labeled beads. These nanoparticles and labeled beads can be provided with a unique label that can be identified through appropriate instrumentation such as a flow-through cell, a bead sorter, or an imaging system. Nanoparticles and labeled beads can be used as substrates which can be functionalized with a variety of chemical and biochemical groups, including, but not limited to nucleic acids, proteins and small molecules. These functionalized nanoparticles or beads, which actually range in size from the hundreds of microns to nanometers, can be placed in a suspension, and binding and/or interaction events can be quantified by optical techniques such as fluorescence using conventional fluorescent markers such as Cy3 and Cy5.

The use of nanoparticles and labeled beads in the analysis of biochemical binding events offers several advantages over conventional microarrays. Since binding studies can be carried out using suspensions of particles, issues related to local probe depletion encountered with microarrays can be minimized. The use of nanoparticles or labeled beads together with multiwell microtiter plates facilitates the design of highly multiplexed assays involving the binding of many different probes to many different particle types within individual wells. Although the use of nanoparticles or labeled beads offers many advantages, the manufacture of such miniaturized devices has proven difficult. More specifically, the mass production of such devices in large quantities and at a low cost is particularly problematic.

One way of manufacturing these miniature devices has been developed by SurroMed, Incorporated, Mountain View, Calif., and involves making cylindrical metal nanoparticles of which the composition along the particle length can be varied in a stripe-like manner. Varying the number of stripes, the width of stripes, the identity of the metals, and the overall particle shape enables the production of a wide variety of unique labels. These "nanobarcode" tags can be identified using conventional optical microscopy, based on the pattern of differential reflectivity of adjacent metal stripes. These identification tags facilitate multiplexing of assays in various media. However, the manufacture of these metallic nanoparticles can be technically challenging and expensive. In addition, reflectance measurements generally have a high signal to noise ratio and poor sensitivity.

A method for manufacturing microparticles is described in U.S. Pat. No. 6,268,222. U.S. Pat. No. 6,268,222 describes a core particle having on its surface smaller polymeric particles stained with different fluorescent dyes. One limitation of the use of fluorescent dyes to identify the particles is that the excitation and emission spectra of these dyes may interfere or overlap with conventional dyes such as Cy3 and Cy3 that are used for tagging reporter molecules used in bioanalysis. In addition, the fluorescence intensity of dyes tends to deteriorate over time upon prolonged or repeated exposure to light. Still another limitation of dyes is that the degradation products of these dyes are organic compounds that may interfere with biological processes and molecules being evaluated.

It would be advantageous to provide miniaturized labels that could be encoded with a large number of unique identification tags and could be utilized for sensing interaction and binding of molecules. Moreover, it would be desirable if the devices could be mass produced easily and inexpensively. Furthermore, it would be useful if the devices could be identified using conventional optical detection techniques, for example, those using fluorescence detection.

SUMMARY OF INVENTION

One embodiment of the invention relates to a detectable label comprising a particle containing at least one rare earth element. According to another embodiment, the rare earth elements may include Ce, Pr, Nd, Sm, Eu, Gd, Tb, Dy, Ho, Er, Tm, Yb, U, and combinations thereof. In another embodiment, the particle includes a plurality of rare earth elements arranged in a pattern or array to provide a unique identification code for the particle. In other embodiments, the label is adapted to detect an analyte in a sample or interaction of two molecules.

In still other embodiments, the particle includes a glass microparticle such as a microsphere having a pattern of rare earth elements shutter masked thereon. In other embodiments, the particle includes a cross-section of a fiber including an array of layers, at least one of the layers having an optical property different from an optical property of the other layers. In certain embodiments, the layers are arranged concentrically. In other embodiments, the layers are arranged across a cross section of the fiber. In some embodiments, at least one of the layers varies in thickness from other layers in the particle. In another embodiment, the layers in the fiber are arranged concentrically, and at least one of the concentric layers has a spectral emission different from the spectral emission of adjacent concentric layers. The fibers can be made from a variety of materials, including, but not limited to inorganic materials, glasses, polymers and combinations of these materials.

In some embodiments, the particle includes a chemical or biological functional group attached to the particle for interaction with an analyte or biomolecule. According to another embodiment of the invention, the particle includes a surface treatment to facilitate binding or attachment of biomolecules thereto. According to another embodiment, the particle is derived from a cross-section plurality of fibers arranged in a bundle, at least one of the fibers including a rare earth dopant different from the rare earth dopant contained in the other fibers in the bundle.

Another embodiment of the invention relates to a method of detecting an analyte in a sample including the steps of placing the sample in contact with a particle containing at least one rare earth element, the particle including a chemical functional group and a pattern thereon to provide a label for the particle and monitoring the sample for the presence or absence of the analyte. In some embodiments of the method of detecting an analyte, the particle includes a cross section of a glass fiber having a cross-sectional dimension less than about one millimeter. In some embodiments of the method of detecting an analyte, the particle includes a plurality of layers arranged to provide the pattern. In certain embodiments of the method of detecting an analyte, the layers are arranged concentrically, and in other embodiments, the layers are arranged across a cross-section of the particle. In some embodiments of the method of detecting the analyte, at least one of the layers has a different thickness from the other layers. According to some embodiments, at least one of the layers includes a rare earth element having a spectral emission that is different of the spectral emission of the other layers. The layers may be made from materials such as inorganic materials, glasses, polymers and combinations of these materials. In another embodiment of a method of detecting an analyte using a particle doped with a rare earth element, the particle includes a glass microparticle having rare earth elements shutter masked thereon to provide the pattern.

In another embodiment, a method of manufacturing an identifiable label for detecting the presence of an analyte in a sample or interaction of biomolecules is provided. This embodiment includes the steps of drawing a fiber having an array of regions of differing optical properties, the array of regions arranged in a manner to identify the fiber, and contacting the fiber with a chemical or biological functional group selected from the group consisting of a nucleic acid, an antibody, a protein, and an enzyme. Attachment or binding of biomolecules may be facilitated in certain embodiments by providing an appropriate surface treatment or chemistry on the fiber cross section. In another embodiment, the array of regions includes a rare earth element. In another embodiment, the method of manufacturing a label may further include the step of slicing the fiber into a plurality of cross sections. In one particular embodiment, a femtosecond pulsed laser is used to slice the fiber. In some embodiments of this method, the array of regions may be arranged concentrically. In other embodiments, the array of regions may be arranged across a cross section of the fiber. In certain embodiments of the method of manufacturing a label, the cross-section of the fiber is less than 1 millimeter. In certain embodiments of manufacturing a label from a fiber cross section, an array of regions may be provided, and this array of regions may be separated by a dissolvable glass which can be removed after the fiber is manufactured. In other embodiments of manufacturing a label from a fiber cross-section, some layers may be made from glass and some layers may be made from polymers.

Still another embodiment of the invention relates to a method of manufacturing an identifiable label for detecting the presence of an analyte in a sample or interaction of biomolecules including the steps of providing a particle and shutter masking a pattern thereon to provide a unique identification code for the particle. In some embodiments, the pattern may be provided by shutter masking a plurality of rare earth elements on the particle to provide a unique identification code for the particle and contacting the particle with a chemical functional group. Suitable particles may include microspheres such as glass microspheres. In another embodiment, further steps may include the steps of depositing the particles in a microwell plate including a plurality of microwells and selectively depositing rare earth materials in the microwells to provide a unique identification code for the particles contained in each microwell.

Another embodiment of the invention relates to a method of detecting multiple analytes in a sample. This embodiment includes the steps of providing coded particles, each of the particles having an analyte associated therewith, illuminating the particles with a light source, obtaining a spectral image of the particles and utilizing the spectral image to decode the particles. In certain embodiments, the spectral image of each individual particle includes the fluorescent emission from at least two different rare earth elements. In other embodiments, the rare earth elements are arranged in a pattern to provide a unique code for each particle. In some embodiments, the particles are imaged and the pattern is decoded to identify the analyte associated with each particle.

Additional advantages of the invention will be set forth in the following detailed description. It is to be understood that both the foregoing general description and the following detailed description are exemplary and are intended to provide further explanation of the invention as claimed..

BRIEF DESCRIPTION OF THE DRAWINGS

The patent or application file contains at least one drawing executed in color. Copies of this patent or patent application publication with color drawings will be provided by the Office upon request and payment of the necessary fee.

DETAILED DESCRIPTION

Figure 1:
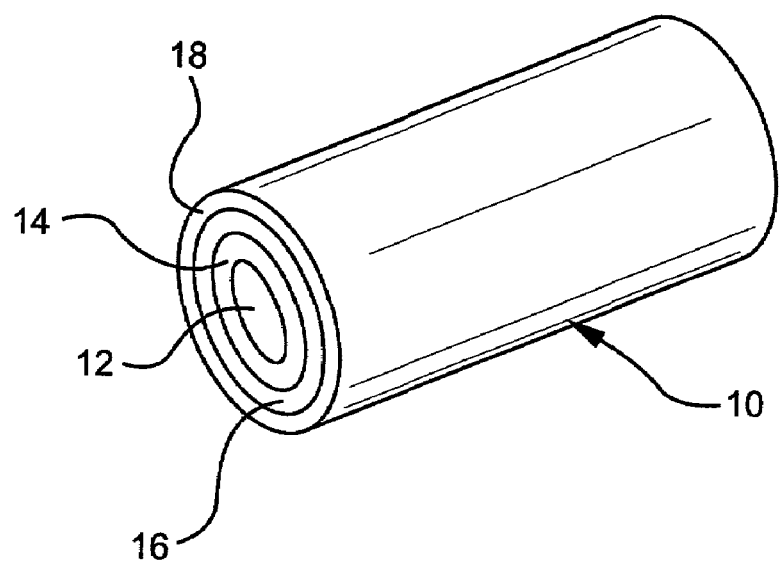
FIG. 1 shows a schematic representation of a label according to one embodiment of the invention.

The present invention relates to miniature particles, their manufacture and use of particles as detectable labels. In some embodiments, the particles are doped with rare earth elements. In certain embodiments, particles can be manufactured by drawing fibers or shutter masking particles such as microspheres and providing a pattern associated with the fiber or microsphere to function as a label for the particle. As used herein, the term label means an identifying or descriptive marker including an encoded particle. The labels and methods of the present invention are useful in fields such as chemical, biochemical, biological or biomedical analysis, process control, pollution detection and control, and other areas. The label and methods are adaptable to a wide variety of samples including biological samples and extracts (such as physiological fluids, nucleic acid and/or protein-containing solutions, microbial cultures, etc.), environmental samples (such as water sources), industrial, especially chemical reagents, products and wastes, etc. According to the present invention, large numbers of particles can be simultaneously probed to determine binding and/or interaction between cells and biomolecules including, but not limited to proteins, antigens and antibodies, and nucleic acids. The particles of the present invention could be used in an unlimited number of assays such as high throughput drug screening and in vitro immunodiagnostics.

One advantage of the present invention is the ability to provide labels used in bioanalysis that produce discrete optical signals that do not spectrally interfere with traditional fluorescent channels such as Cy3, Cy5, Texas Red, FITC, and other fluorescent reporter dyes. Another advantage of the present invention is that by using techniques such as fiber drawing or shutter masking, the particles can be inexpensively and easily mass produced. The particles can contain different amounts or concentrations of rare earth elements to provide a unique identification code for each particle. Another way of providing unique identification code is to dope a particle with a plurality of rare earth elements. The elements can be separated spatially to provide a pattern or array similar to a bar code. Each of the different rare earth elements, or same elements doped at a different concentration or location on the particle provides a discrete optical signal capable of detection by conventional optical equipment and can be used to identify the particle.

Still another advantage of the invention is that the labels and methods of the present invention would not require new or elaborate methods of illumination or detection. Optical signals, including, but not limited to fluorescent signals can be collected by an imaging detector such as a charge coupled device (CCD) camera and image analysis can be utilized to determine quantitative assay data. Other systems that could be used for detection for use with the labels and methods of the present invention include an excitation source, a light filter and a detector array.

The particles of the present invention may be attached or associated with a specific binding molecule so that the particles can be utilized in the detection of biological or chemical compounds and interactions of biomolecules with other biomolecules or chemicals. Attachment or association of the particles of the present invention to chemicals or biomolecules can be accomplished using techniques known in the art. An advantage of certain embodiments of the present invention is that in embodiments in which the particles are made from glasses or polymers, attachment of biomolecules and functionalization of such surfaces with coatings or layers with chemicals to facilitate attachment of biomolecules is well-known. For example, coating of glass and polymeric surfaces such as high density microarray and microwell surfaces to promote binding or attachment of biomolecules is known in the art. The surfaces of both organic and inorganic substrates can be modified by the deposition of a polymeric monolayer coating or film to construct biomolecular assemblies. In addition, surface modification can also be used to promote adhesion and lubrication, modify the electrical and optical properties of the substrate surface, and create electroactive films suitable for various optical and electronic sensors and devices. Compounds with amine functionality have found extensive application in the preparation of surfaces for nucleic acid hybridization. Due to their ability to bond to a substrate with a hydroxide and their ability to bond to nucleic acids with an amine, silane compounds are useful as surface coatings that will effectively immobilize nucleic acids. One example of a silane used for biological assay preparation is gamma amino propyl silane (GAPS), which may be deposited by a variety of methods, including CVD, spin coating, spray coating and dip coating. It will be understood that the particles used in accordance with the present invention can be functionalized with virtually any surface chemistry compatible with the particle surface, and the invention is not limited to a particular surface chemistry. In embodiments in which the particles are made from glass, the particles are extremely durable in organic solvents such as ethanol, isopropanol, chloroform, dimethylsulfoxide, dimethylformamide and hexane. Glass particles do not swell or dissolve in such solvents.

According to one embodiment of the invention, the particles are made from a fiber, and the fiber can be encoded to provide a unique identification code for a large number of individual particles. Preferably, according to the present invention, more than 1000 codes, and preferably more than 10,000 unique codes can be provided. The present invention also provides a relatively simple process to mass produce such particles from inexpensive and readily available materials, processes and equipment.

Referring to FIG. 1, according to one embodiment of the invention, a particle can be provided by manufacturing a core 10 made from a glass, a polymer, or any material that can be substantially deformed and drawn into a fiber or ribbon fiber. As used herein, the term "fiber" means an elongate, threadlike or ribbon-like structure. Preferably, the fiber has a cross-sectional dimension of less than 1 millimeter. In embodiments in which the fiber is a ribbon fiber, preferably the ribbon fiber has a cross-sectional dimension less than one millimeter in at least one direction.

Techniques for manufacturing fibers or ribbon fibers are well-known. For example, fibers can be manufactured according to known optical fiber manufacturing techniques in which a preform of a glass or polymeric material is drawn into a fiber by heating one end of the preform to the softening point of the preform material and drawing fiber from the heated end. Fibers can also be manufactured by other known fiber making techniques. According to one aspect of the invention, the core material is covered with concentric layers that have an optical property that is different from an optical property in adjacent layers. The optical properties can be varied by techniques including, but not limited to changing the composition of the layers, doping the layers with, for example, a rare earth element, or varying the colors of each layer. The different optical property can be detected by spectral analysis or any suitable method. As shown in FIG. 1, the core 10 is surrounded by four concentric layers 12, 14, 16, and 18. It will be understood, however, that the invention is not limited to any number of layers or configuration of layers.

In another embodiment of the invention, the thickness of the concentric layers 12, 14, 16 and 18 surrounding the core 10 can be varied. By varying the optical properties and thickness of the layers, and alternating layers having different optical properties and thicknesses, a wide variety of uniquely coded fibers can be manufactured. After generation of a preform including the various layers, the preform can be drawn into fiber having a diameter or cross sectional dimension less than about one millimeter, and preferably on the order of about 10 to 100 microns. Thereafter, the fiber can be sliced or cut into thin sections, having a thickness ranging from about a ten millimeters down to about 1 micron. The slicing or cutting can be accomplished using conventional cutting tools or a laser.

In one particular embodiment, the fiber ribbon can be cut by means of exposure to a femtosecond (fs) pulsed laser operating at about 800 nm or shorter. Experimentation has indicated that longer pulsed lasers result in heating and deformation of the thin fiber ribbon, while fs pulses are so short that the material is ablated from the cut without any heating or deformation of the ribbon. In one experiment, scribes were made 100 um apart along the longitudinal axis of the fiber, and the pieces cleanly fractured into slices with light mechanical pressure. The coded fiber particles also remained in tact without loss of any sections of the fiber. This method could be used to slice the fiber as it is pulled off the draw to economically produce millions of bar code particles per minute. This is just one method of cutting the fiber ribbon. It will be understood that slicing of the fiber could also be performed via gang sawing, photoresist and etching, scribing, or a variety of mechanical techniques.

A single fiber having a length of just a few meters is sufficient to provide millions of slices of fiber having a central core surrounded by concentric layers having varying optical properties, colors, and/or thicknesses. Using well-known optical fiber production and drawing techniques, it is possible to draw miles of fiber from a single preform, which enables the inexpensive and simple production of a very large number of uniquely coded slices.

These uniquely coded slices can be used in a wide variety of sensing and labeling applications. For example, after preparation of the fiber slices, which have a unique identification code based on the optical properties, order and thickness of the slices, the slices can be placed in contact with a chemical functional group for further analysis. For example, each slice could be associated with an analyte such as an antibody, a target DNA, a pharmaceutically active compound, a drug compound, etc. The particles associated with various analytes could then be used in a wide variety of assay formats, for example, where the binding and/or interaction of one or more molecules are being measured through the tagging of one of the reactants with a unique code, and the other reactant with a simple label. Attachment and binding of biomolecules may be facilitated by providing an appropriate surface chemistry on a surface of the particles.

Figure 2:
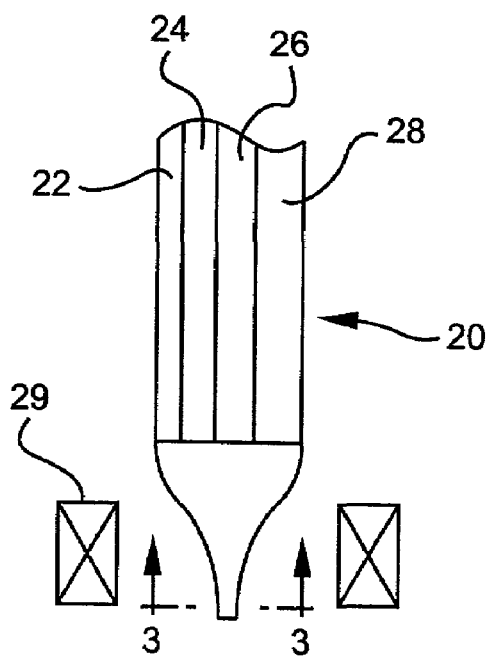
FIG. 2 shows a schematic representation a step used in the manufacture of a label according to another embodiment of the invention.

In another embodiment of the invention, a fiber or ribbon fiber can be prepared that has an array of layers arranged in a row across a cross sectional dimension of the fiber, wherein at least one of the layers has an optical property that is different from an optical property of adjacent layers. As shown in FIG. 2, a preform 20 is assembled that includes elongate sections 22, 24, 26, and 28, and each of the elongate sections has an optical property that is different from an optical property of adjacent layers. According to one aspect of the invention, each of the sections 22, 24, 26 and 28 may include a different dopant, for example, a fluorescent material, to provide a patterned array across a cross section of the perform. In another aspect, the width of each section 22, 24, 26 and 28 can also be varied to increase the number of variables available to provide a unique identifier for each preform. The sections 22, 24, 26, and 28 can be fused together by heating the sections near the softening point of the materials that make up the preform. A fiber can be made by heating the end of the perform 20 in a furnace 29 or other appropriate heating element and drawing an end of the preform 20 so that the preform necks down to a fiber or ribbon fiber.

Figure 3:
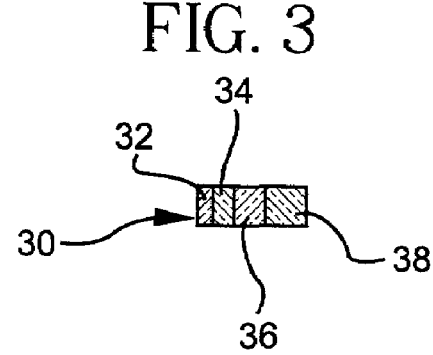
FIG. 3 shows a schematic representation of a cross-section of a particle made according to FIG. 2, taken along line 3—3 of FIG. 2.

As shown in FIG. 3, a particle 30, made from preform 20 includes miniaturized sections 32, 34, 36 and 38, each of the sections having a width and an optical property that varies from the width and an optical property of adjacent sections. By manufacturing particles in this manner, a uniquely coded bar code pattern can be provided for each group of particles made from the preform. The fiber and resulting particle may have a cross-sectional diameter as small as a few nanometers or a large as a few millimeters.

Figure 4A:
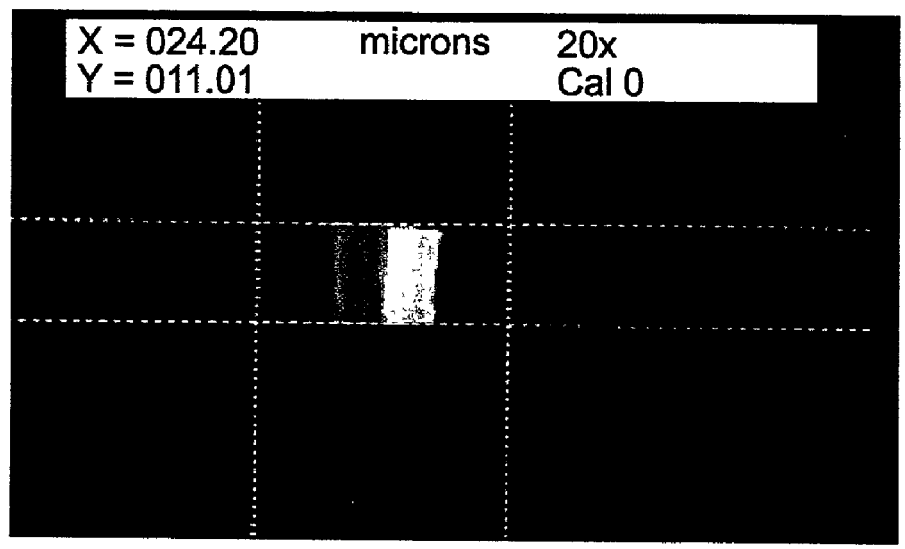
FIGS. 4a and 4b are microphotographs of particles according to one embodiment of the present invention.
Figure 4B:
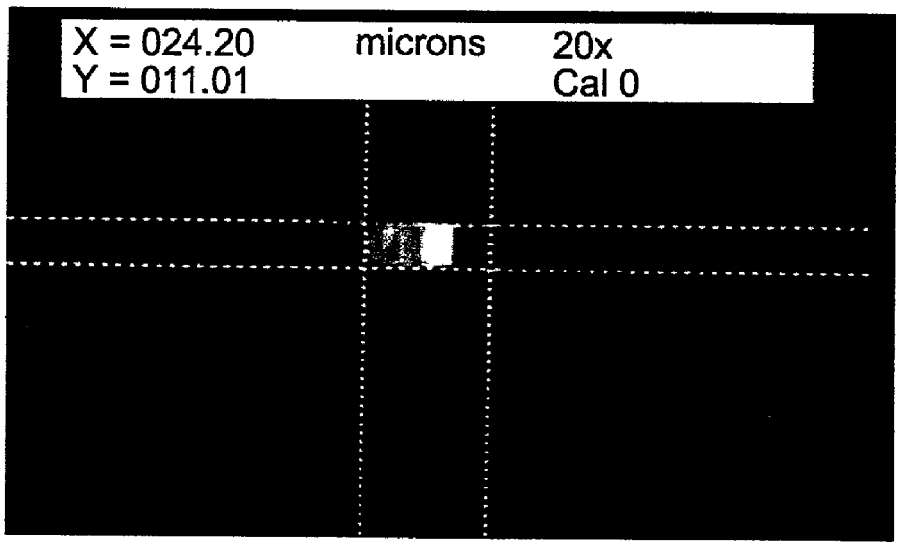

A particle made from a fiber that has an array or bar code pattern across a cross sectional dimension of the fiber including, can be used as a detectable label that can be detected by a scanner or a suitable detector. For example, glasses that fluoresce red, green and blue can be assembled together to provide a fiber preform including longitudinal "stripes" of varying optical properties. The glass preform can then be drawn into a fiber or ribbon using conventional drawing techniques. FIGS. 4a and 4b show examples of particles that were manufactured by drawing fibers and slicing the fibers into particles. Referring to FIG. 4a, a particle having a cross-sectional dimension of about 50 microns and a height of about 25 microns is shown. In FIG. 4b, a particle having a cross-sectional dimension of about 25 microns and a height of 11 microns is shown. The particles shown in FIGS. 4a and 4b include dopants that fluoresce red, blue and green. By using a variety of rare earth dopants and combinations of rare earth dopants, the spectral emission can be varied.

In another aspect of the invention, multiple glass sections that provide an array or bar code pattern with different optical properties can be assembled together with a dissolvable glass such as $B_2O_3$ separating the individual sections. After the stacked preforms are drawn into a fiber and sliced into individual particles, the dissolvable glass can be removed with an appropriate solvent. For example, if $B_2O_3$ is provided between the sections, the $B_2O_3$ can be dissolved with water or acid. By using this technique, a fiber as small as 5 nm could be manufactured. In still another embodiment, a composite fiber could be made by using sections made from glass and sections made from polymers. After manufacture of the fibers, they could be cut into pieces of desired length by gang sawing, scribing and breaking, mechanical chopping or any other appropriate method.

Figure 5:
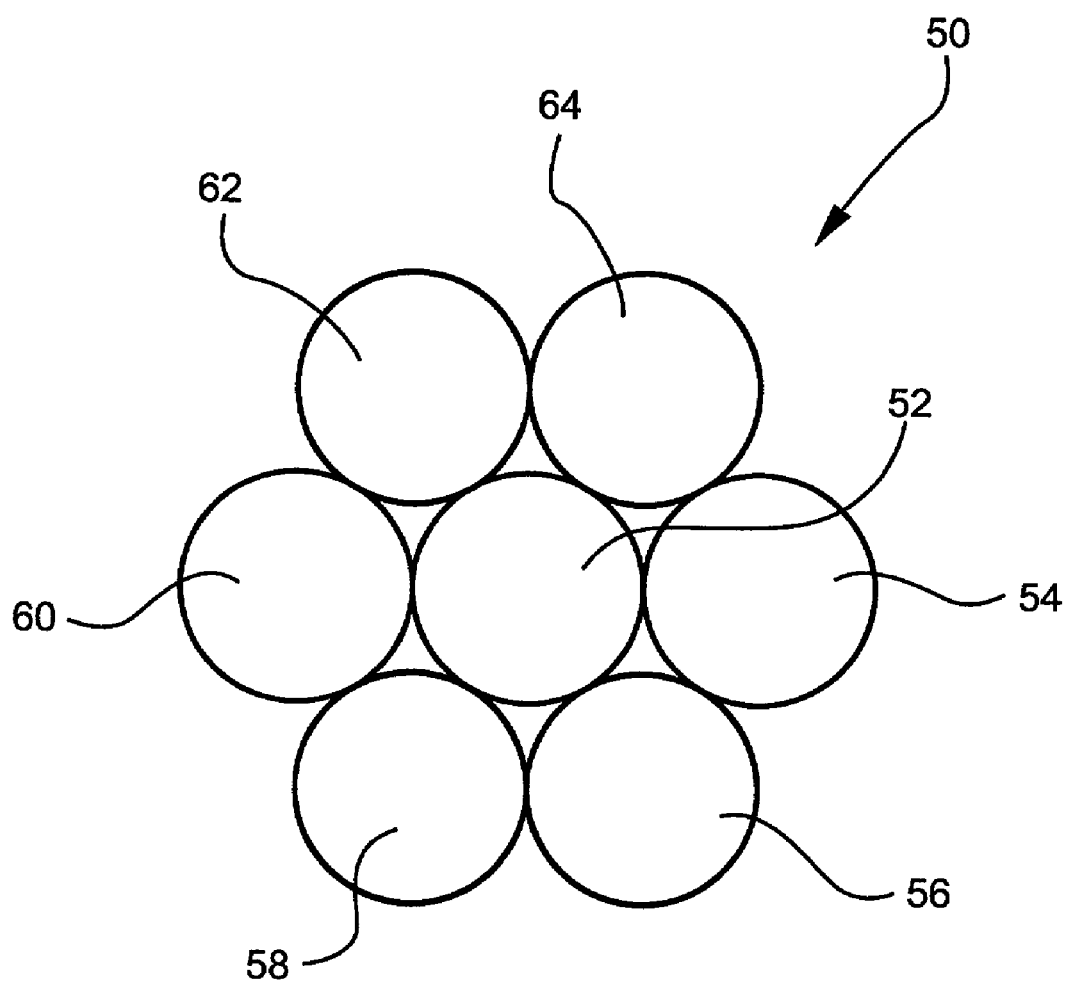
FIG. 5 is a cross-sectional view of a particle according to another embodiment of the invention.

In still another embodiment of the invention, a particle according to the present invention could be provided by coaxially assembling an array of rod-shaped preforms around a central rod and drawing the array into a fiber that could then be cut or sliced into a particle. In still another embodiment, individual fibers could be coaxially disposed around a central fiber, fused, and sliced to provide a particle. At least one of the individual sections could have a different optical property from the other sections. In another embodiment, the diameter of the individual fibers could be varied. A cross-sectional view of a particle made in this manner is shown in FIG. 5. The particle 50 includes a central section 52 surrounded by sections 54, 56, 58, 60, 62 and 64.

In another embodiment of the invention, shutter masking techniques can be utilized to produce particles having a plurality of rare earth elements deposited on the particles. Shutter masking techniques are known, and the concept of shutter masking can be applied to manufacture of labels made from particles such as microspheres to produce over 1000 different types of particles. For example, 1024 different types of labeled silica spheres such as manufactured by GelTech, Inc. with a size of approximately 1.5 m could be manufactured in 10 steps. Unlabeled silica spheres would be placed into the 10 L wells of a 1536 plate (Corning, Inc.).

The label would be applied through a mask by such sol-gel, CVD, or other suitable process.

Figure 6A:
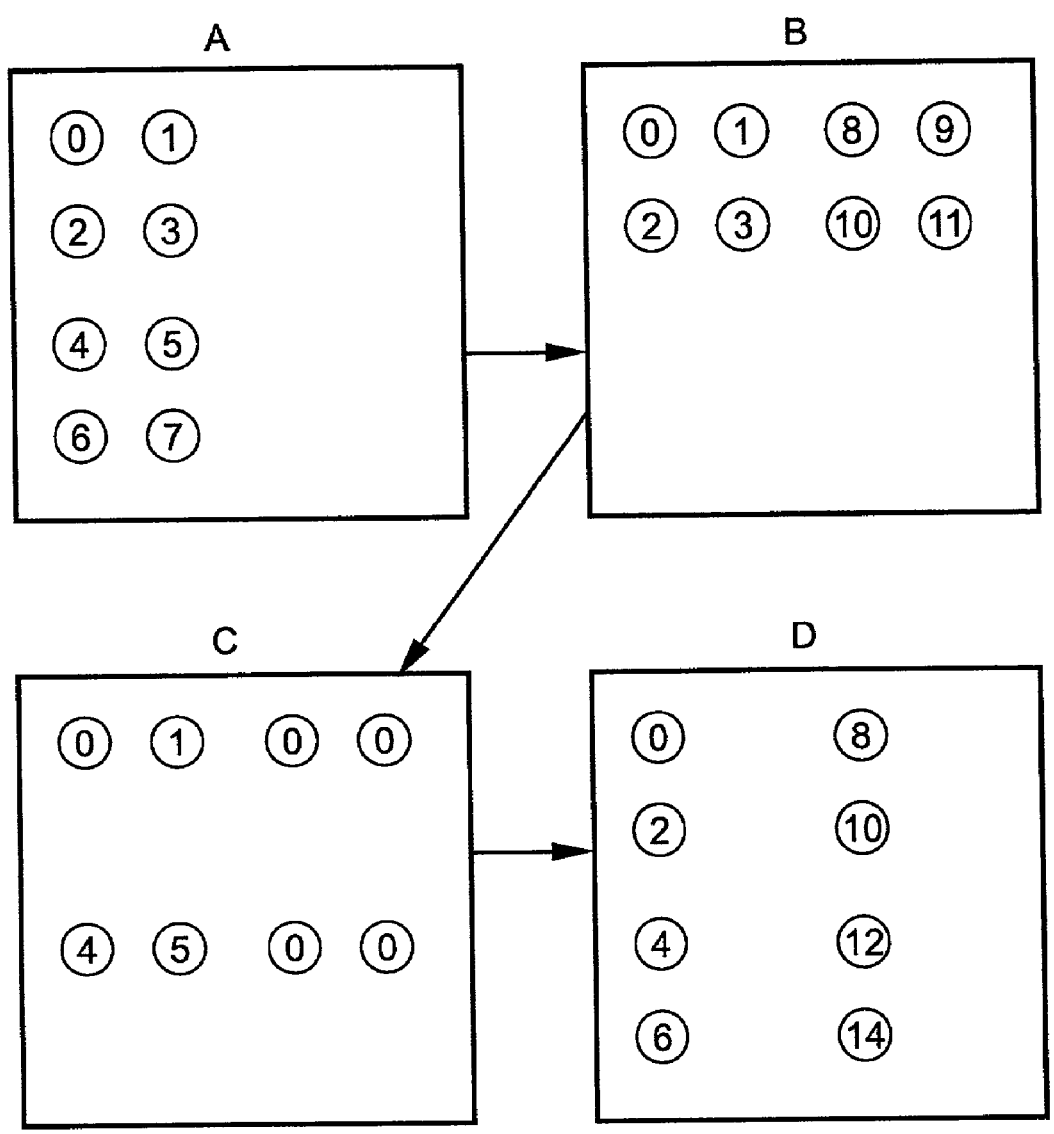
FIGS. 6a and 6b shows steps of shutter masking a pattern on a particle according to another embodiment of the invention.
Figure 6B:
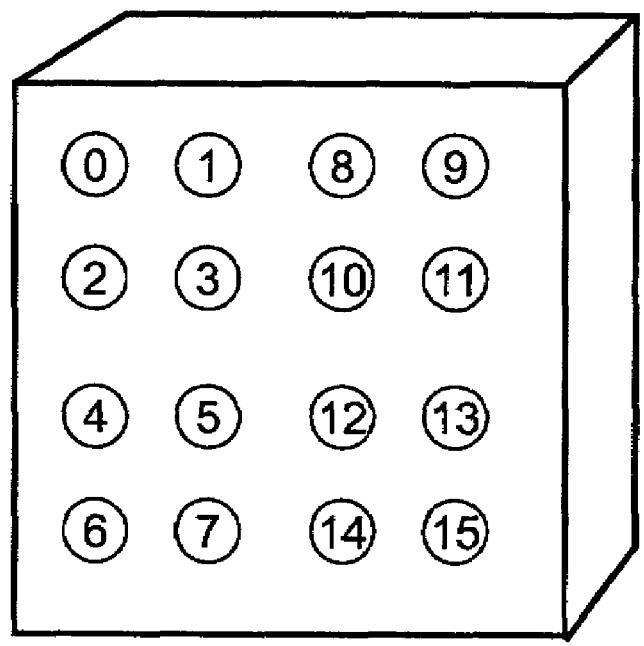

For the purposes of illustration, a representative four step masking procedure is shown in FIG. 6. It will be understood that the present invention is not limited to any particular number of steps or the use of any particular type of microwell plate. Referring to FIGS. 6a and 6b, a four step masking process could be used to create 16 different types of particles labeled with combinations of markers A, B, C, and D in a 4×4 well plate. A, B, C, and D be fluorescent rare earth elements applied by PVD, CVD, etc or other appropriate markers. In this example, order is not used to distinguish particle types, only presence or absence of the marker. Shutter masking can be extended to make particles in which intensity and order of markers is used for identification, as well. In a first step, particles or microspheres contained in wells 0, 1, 2, 3, 4, 5, 6, and 7 are doped with marker A, while wells 8, 9, 10, 11, 12, 13, 14 and 15 are masked. Next, marker B is deposited on the particles or microspheres in wells 0, 1, 2, 3, 8, 9, 10 and 11, while wells 4, 5, 6, 7, 12, 13, 14 and 15 are masked. Then, marker C is added to wells 0, 1, 4, 5, 8, 9, 12, and 13, while wells 2, 3, 6, 7, 10, 11, 14 and 15 are masked. Then, marker D is added to wells 0, 2, 4, 6, 8, 10, 12, and 14, while wells 1, 3, 5, 7, 9, 11, 13, and 15 are masked. FIG. 6b shows the marking applied to the particles contained in each of the wells, wherein X represents no marker. As shown in FIG. 6b, the particles or microspheres in each of the wells would be marked as follows:

| Well Number | Marking |
|---|---|
| 0 | ABCD |
| 1 | ABCX |
| 2 | ABXD |
| 3 | ABXX |
| 4 | AXCD |
| 5 | AXCX |
| 6 | AXXD |
| 7 | AXXX |
| 8 | XBCD |
| 9 | XBCX |
| 10 | XBXD |
| 11 | XBXX |
| 12 | XXCD |
| 13 | XXCX |
| 14 | XXXD |
| 15 | XXXX |

In another embodiment of the invention, a method of detecting multiple analytes in a sample is provided by using spectral imaging. Spectral imaging is a technique in which the spectral properties of every point or pixel in an image are captured. For example, when many fluorescent coded microparticles are excited and in the field of view, the emission spectra (as a function of wavelength) of every pixel in the image is captured. Thus non overlapping peaks can be easily resolved and simple computer algorithms can be used to decode or interpret the identities of all the coded particles in the field of view. Using spectral imaging, the spectra at each point can be acquired, and the composite image obtained directly in a single scan via a computer algorithm. When combined with the coded particles of the present invention that can all be excited with the same light source, the resulting spectral image can be used to decode all of the coded particles with one image. Thus spectral imaging can simplify measurements and increase throughput as well as enable unique analysis of assays in which multiple tags or coded particles are present.

Figure 7A:
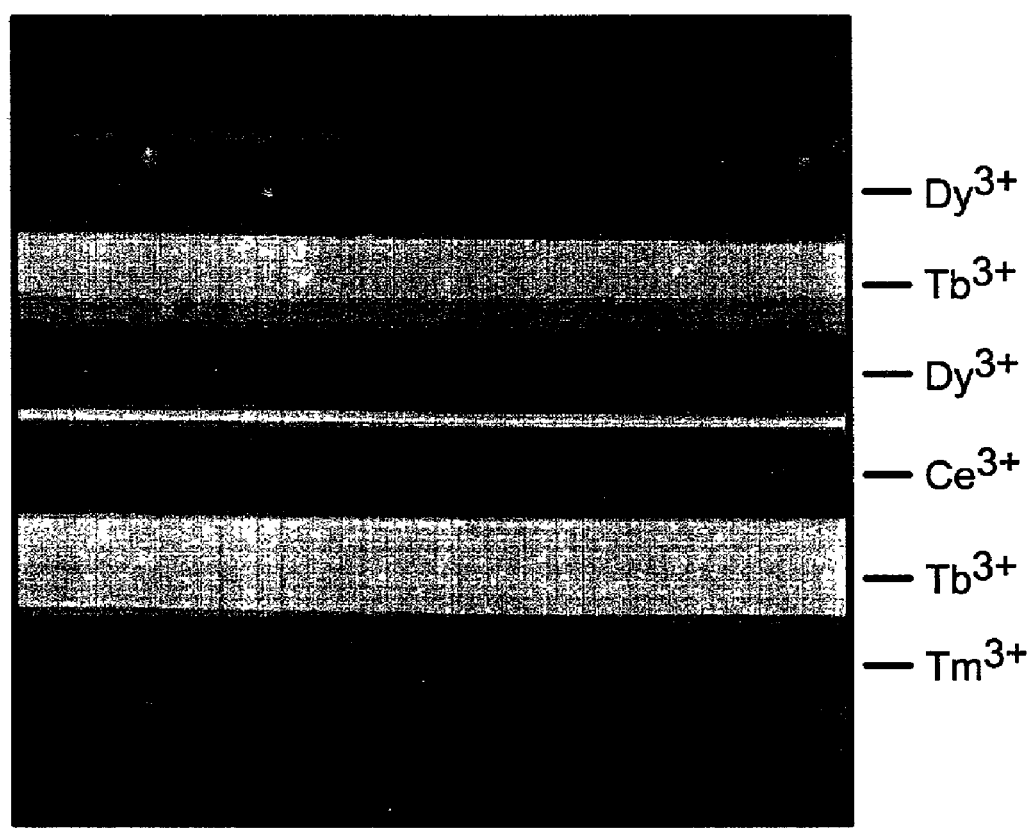
FIG. 7a is a microphotograph of an encoded particle produced according to one embodiment of the invention.
Figure 7B:
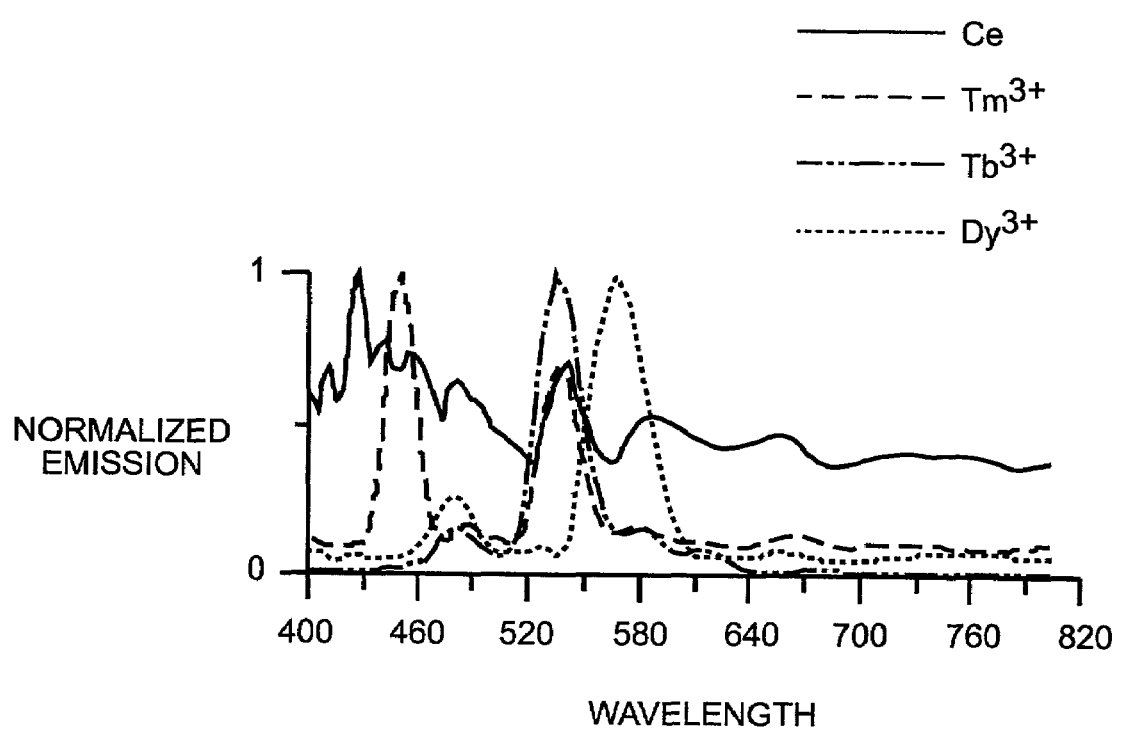
FIG. 7b is a plot of the emission spectra of the particle shown in FIG. 7a after illumination with an ultraviolet light source.

In one spectral imaging experiment, a coded particle or label made from a fiber ribbon shown in FIG. 7a and having a cross-section of about 1 mm was decoded with a hand-held UV lamp and a spectral imaging microscope. The coded glass particle shown in FIG. 7a was made using ribbon drawing techniques described in the Example below. The particle included sections or "channels" of Tm, Tb, Ce, Dy, Tb and Dy. A 4 mW 365 nm Hg lamp was used to illuminate the particle and the fluorescence was detectable from all 6 sections or channels in the particle. Even more importantly, the four colors of the coded particle or label were also spectrally resolvable. FIG. 7b shows the "decoded" ribbon in which the emission spectra were used to decode the fluorescent image of the ribbon and assign a selected false color to any pixel in the image matching the reference spectrum. According to the present invention, labels or coded particles can be decoded using a simple computer algorithm and an inexpensive 4 mW unfocused UV lamp.

It will be understood, of course that this relatively simple experiment is exemplary of the present invention, and more elaborate spectral imaging systems can be designed by those of skill in the art. Indeed, this simple technique did not work very well on a 50 micron diameter fiber due to its lower absorption cross section and smaller signal. However, the microscope objective lens also precluded close proximity of the UV lamp. Using a microscope with a built-in, focused UV light source should be sufficient to decode smaller fibers. Alternatively, the absorption cross section of the fiber can be increased by increasing the dopant levels (at the sacrifice of quantum efficiency) or adding a sensitizer like Ce to absorb the UV and transfer it to the fluorescent ion.

Without intending to limit the invention in any manner, the present invention will be more fully described by the following example.

EXAMPLES

Tables I and II below show exemplary glass compositions that can be used to make a fluorescent bar code fiber in accordance with one embodiment of the invention. The glass compositions in Table I and Table II were chosen because fluorescent rare earth materials are soluble in these glasses. It will be understood, however, that the present invention is not limited to a particular glass composition, and that the fibers of the present invention could be made from other suitable materials such as polymers or metals.

TABLE I

| Composition (Weight %) | 1 | 2 | 3 | 4 |
|---|---|---|---|---|
| $SiO_2$ | 50.61 | 51.22 | 52.65 | 52.40 |
| $Al_2O_3$ | 14.56 | 14.73 | 15.14 | 15.07 |
| $B_2O_3$ | 7.39 | 7.49 | 7.70 | 7.66 |
| MgO | 0.64 | 0.65 | 0.67 | 0.67 |
| CaO | 3.65 | 3.70 | 3.79 | 3.78 |
| SrO | 1.67 | 1.69 | 1.73 | 1.72 |
| BaO | 8.24 | 8.34 | 8.57 | 8.54 |
| $Eu_2O_3$ | 6.58 | 0 | 0 | 0 |
| $Tb_2O_3$ | 0 | 6.93 | 0 | 0 |
| $CeO_2$ | 0 | 0 | 0.23 | 0 |
| $Tm_2O_3$ | 0 | 0 | 0 | 0.99 |
| $Y_2O_3$ | 0 | 0 | 4.11 | 3.79 |
| $Sb_2O_3$ | 1.45 | 0 | 0 | 0 |
| F | 0.24 | 0.24 | 0.24 | 0.24 |

The glass compositions above were melted in 1 kg batches overnight at 1650° C., stirring, and then pouring a fine stream of the molten glass into a bucket of water to make cullet. The cullet was then remelted for 4 hrs at 1650° C. and poured into a 25×25×200 mm steel mold and annealed at 775° C. for 1 hour to provide glass bars. This two step melting process improved glass homogeneity and quality, minimizing cord, bubbles, and stria in the glass.

The individual glass bars were then drawn into 3 mm square canes at about 1170° C. and 250 mm/min. A single cane from each composition was stacked together longitudinally with a cane from each of the other compositions to form an array or a master preform including layers having different fluorescent properties similar to the arrangement shown in FIG. 2. The master preform was prefused together at 950° C. in a graphite mold to hold them in place. The prefused preform was then drawn into ribbon fiber at 1200° C. at 0.25 m/s.

TABLE II

| Composition (Weight %) | 5 | 6 | 7 | 8 |
| --- | --- | --- | --- | --- |
| $SiO_2$ | 55.46 | 55.31 | 59.53 | 59.69 |
| $Al_2O_3$ | 0.96 | 0.95 | 1.03 | 1.03 |
| $Li_2O$ | 1.60 | 1.60 | 1.72 | 1.72 |
| $Na_2O$ | 3.32 | 3.31 | 3.56 | 3.57 |
| $K_2O$ | 5.04 | 5.03 | 5.41 | 5.43 |
| SrO | 9.70 | 9.67 | 10.41 | 10.44 |
| BaO | 10.25 | 10.23 | 11.01 | 11.03 |
| ZnO | 6.54 | 6.52 | 7.01 | 7.03 |
| $Eu_2O_3$ | 7.06 | 0 | 0 | 0 |
| $Tb_2O_3$ | 0 | 7.32 | 0 | 0 |
| $CeO_2$ | 0 | 0 | 0.25 | 0 |
| CaO | 0.01 | 0.01 | 0.01 | 0.01 |

The glass compositions above were melted in 1 kg batches for three hours at 1500° C., stirred and poured into a 25×25×200 mm steel mold and annealed at 525° C. for 1 hour to provide glass bars.

The individual glass bars were then drawn into 3 mm square canes at about 1000° C. and 250 mm/min. A single cane from each composition was stacked together longitudinally with a cane from each of the other compositions to form an array or a master preform including layers having different fluorescent properties similar to the arrangement shown in FIG. 2. The master preform was prefused together at 700° C. in a graphite mold to hold the sections in place. The prefused preform was then drawn into ribbon fiber at 1050° C. at 0.25 m/s.

In each of the samples prepared above, the section of fiber doped with $Eu_2O_3$ produced red fluorescence, the sections of fiber doped with $Tb_2O_3$ fluoresced green, and the section of fiber doped with $Tm_2O_3$ and $CeO_2$ fluoresced blue. These dopants are exemplary only, and a wide variety of other dopants could be used in accordance with the present invention. In addition, mixtures of dopants could be used to produce a wider variety of fluorescent colors. The glasses produced in this Example can be excited with a mercury lamp at either 254 or 365 nm. At these wavelengths, fluorescent tags such as the commonly used Cy-3 and Cy-5 are not excited, and therefore, crosstalk and interference between identifiers in the fibers and DNA labels is not an issue.

Any suitable detection system can be utilized to detect the difference in optical properties between the layers of the sensors of the present invention. For example, in a simple system, a microscope could be utilized. Other systems could utilize a solid state detector, a photomultiplier tube, photographic film, or a CCD device used together with a microscope, a spectrometer, a luminometer microscope, a fluorescence scanner, or a flow cytometer. A wide variety of optical properties can be varied in the layers according to the present invention. Such optical properties include, but are not limited to difference in emission maxima, difference in fluorescent intensity, difference in wavelength of emission, difference of fluorescent polarization, and combinations of these properties. The invention is widely adaptable to a variety of sensing applications, including, but not limited to, clinical, forensics, genetic analysis, biomolecular analysis and drug-discovery efforts.

It will be apparent to those skilled in the art that various modifications and variations can be made to the present invention without departing from the spirit or scope of the invention. Thus, it is intended that the present invention cover modifications and variations of this invention provided they come within the scope of the appended claims and their equivalents.

What is claimed is:

1. A detectable label comprising a glass particle doped with a plurality of rare earth elements, which are arranged in a pattern or array to provide a unique identification code to identify a functional group attached thereto, wherein the functional group is selected from the group consisting of a nucleic acid, an antibody, a protein, and an enzyme, and wherein the rare earth element is selected from the group consisting of Ce, Pr, Nd, Sm, Eu, Gd, Tb, Dy, Ho, Er, Tm, Yb, U, and combinations thereof, and whereby the particle has a diameter of between 10 microns and 100 microns;

and the particle is a fiber having a cross-section including an array of layers, each of the layers having an optical property different from an optical property of adjacent layers.

2. The label of claim 1, wherein the fiber includes materials selected from the group consisting of inorganic materials, glasses, polymers and combinations thereof.

3. The label of claim 1, wherein the layers are arranged concentrically.

4. The label of claim 3, wherein one of the concentric layers varies in thickness from the other layers.

5. The label of claim 1, wherein the layers are arranged across the cross section of the fiber.

6. The label of claim 5, wherein one of the layers varies in thickness from the other layers.

7. The label of claim 1, wherein the layers are arranged concentrically, and each concentric layer has a spectral emission different from the spectral emission of adjacent concentric layers.

8. The label of claim 1, wherein the particle is made from glass, the layers are arranged across a cross section of the fiber and at least one of the layers has a spectral emission different from the spectral emission of the other layers in the particle.

9. The label of claim 1, wherein the particle includes a chemical functional group attached thereto for interaction with an analyte or biomolecule.

10. The label of claim 9, wherein the particle includes a surface treatment to facilitate binding or attachment of biomolecules thereto.

11. The label of claim 1, wherein the particle includes a chemical or biological functional group attached thereto for interaction with the analyte.

12. The label of claim 1, wherein the layers are arranged in a manner that can be used to identify the functional group.

13. The label of claim 12, wherein the fiber is made from glass, and the layers are doped with elements selected from the group consisting of Ce, Pr, Nd, Sm, Eu, Gd, Tb, Dy, Ho, Er, Tm, Yb, U, and combinations thereof.

14. The label of claim 1, wherein the fiber has a cross-sectional dimension of less than 1 millimeter.

15. The label of claim 1, wherein the particle is derived from a cross-section of a plurality of fibers arranged in a bundle, and at least one of the fibers including at least one rare earth dopant different from the rare earth dopant contained in at least one of the other fibers in the bundle.

* * * * *